United States Patent [19]

Mugnier et al.

[11] Patent Number: 4,599,312

[45] Date of Patent: Jul. 8, 1986

[54] METHOD OF PRODUCING ENDOMYCORRHIZIAN FUNGI WITH ARBUSCULES AND VESICLES IN VITRO

[75] Inventors: Jacques Mugnier, Paris; Gerard Jung, Leuville/Orge; Jean-Louis Prioul, Les Ulis, all of France

[73] Assignee: Rhone-Poulenc Agrochimie, Lyons, France

[21] Appl. No.: 505,276

[22] Filed: Jun. 17, 1983

[30] Foreign Application Priority Data

Jun. 21, 1982 [FR] France ................... 82 10768

[51] Int. Cl.⁴ .................. C12N 15/00; C12N 1/14; C12N 1/00; C12N 5/00; A01B 79/00
[52] U.S. Cl. ....................... 435/172.3; 435/254; 435/317; 435/240; 47/58
[58] Field of Search ............ 435/254, 172.3, 68, 435/317, 42; 47/58

[56] References Cited

U.S. PATENT DOCUMENTS 4,294,037  10/1981  Mosse et al. ............... 47/59

OTHER PUBLICATIONS

White, et al 1982, "Tumor Induction by Agrobacterium Rhizogens Involves the Transfer of Plasmid DNA to the Plant Genome" Proc. Natl. Acad. Sci., vol. 79, pp. 3193–3197.

Murashige 1979, "Plant Tissue Culture and its Importance to Agriculture" in *Practical Tissue Culture Applications*, Academic Press, Inc., pp. 27–44.

Rhodes, 1983 "Mycorrhizae" in *Handbook of Plant Cell Culture*, Evans, Sharp, Ammirato & Yamada, Eds. MacMillan Publ. Co., NY, (vol. 1).

*Primary Examiner*—Thomas G. Wiseman
*Assistant Examiner*—Joanne M. Giesser
*Attorney, Agent, or Firm*—Burns, Doane, Swecker & Mathis

[57] ABSTRACT

Provided is a method of obtaining endomycorrhizian fungi with vesicles and arbuscules in vitro. The method comprises producing dicotyledone roots which have been genetically converted by inserting genes of root inducing or tumor inducing plasmid into the genome of dicotyledone roots, and then inoculating the converted roots with endomycorrhiza spores. Application of the present method can be very useful in agriculture and horticulture.

39 Claims, 5 Drawing Figures

FIG. 4

Fig. 5

METHOD OF PRODUCING ENDOMYCORRHIZIAN FUNGI WITH ARBUSCULES AND VESICLES IN VITRO

BACKGROUND OF THE INVENTION

1. Field of the Invention

The invention relates to a method of obtaining endomycorrhizian fungi with vesicles and arbuscules (VAM) in vitro. More specifically, the present invention relates to the inoculation of genetically converted dicotyledon roots with endomycorrhiza spores.

2. Description of the Prior Art

Recent developments in research pertaining to endotrophic mycorrhizas (endomycorrhizas) have shown their use in agriculture and horticulture to have great potential importance. These endophytic fungi are far from the most common, but come into symbiosis with virtually all cultivated plants. They are also characterized by at least three basic properties:

(i) their association with a plant is essential to their own development,
(ii) they have a wide range of host plants, and no specificity has so far been recorded, and,
(iii) they stimulate growth of the plants which they infect.

The favorable effect on the host plant is a well established fact. It is due to an increase in absorption of inorganic ions by the mycorrhized plant, and more particularly, the absorption of relatively immobile ions and chiefly phosphorus ones. It has been demonstrated that the hyphas of the endomycorrhizogenic fungus are capable of absorbing soluble phosphorus, transporting it and transferring it to the plant. These processes lead to improved growth of the mycorrhized plant. See, for example, GIANINAZZI S., 1976 *Physiol. Veg.*, Vol. 14, 733–741.

Furthermore, it has been observed that infection by an endomycorrhizian fungus may protect the roots of the mycorrhized plant from pathogens in the soil. For example, see, BALTRUSCHAT H., 1975, *Phytopathol*, Vol. 84, 172–188.

However, despite the large amount of work carried out to date, e.g., RHODES L. H., 1980, *Outlook Agricult.*, Vol. 10, 275–281; HAYMAN D. S., 1980 *Nature*, Vol. 287, 487–490, the main difficulty in applying endotrophic mycorrhizas is that it is not known how to produce them in large quantities for commercial application. It is believed that no one has ever succeeded in cultivating them in a sterile medium without the host plant.

Unlike most symbiotic micro-organisms which are parasitic or saprophytic, VAM fungi cannot be cultivated in vitro. Note, BARRET J. T., 1947, *Phytopathol.*, Vol. 37, 359; MOOSE B., 1962, *J. Gen. Microbiol.*, Vol. 27, 509–520; HARLEY J. L., 1965, *Ecology of Soil-Borne Plant Pathogens*, Baker and Snyder Eds., Univ. California Press, 218–229; HEPPER C. M., 1979, *Soil Biol. Biochem.*, Vol. 11, 269–277; HEPPER C. M., 1981, *New Phytol.*, Vol. 88, 641–647. The large number of attempts at mycorrhization which have been carried out so far have consisted of using inoculums prepared from complete plants which are cultivated in pots or a greenhouse. Inoculation is nearly always carried out with specially gathered mycorrhized roots, or sometimes with a suspension of spores. JACKSON et al, 1972, *Proc. Soil Sci. Soc. Am.*, Vol. 36, 64–67, used lyophilised roots, while HALL, 1979, *Soil Biol. Biochem.*, Vol. 11, 85–86, recommends using soil pellets mixed with infected roots.

In all cases, one of the problems encountered is the possibility of introducing contaminants into the soil through inoculation of the VAM, particularly when for reasons of plant health it is necessary to disinfect the soil before planting, thereby resulting in destruction of the VAM naturally present. Moreover, the time required to produce an inoculum is generally two-four months, which is long enough to produce many contaminants. Such problems have hindered commercialization of the inoculums. In addition, the inoculums cost at least as much as, or more than, the fertilizers which would be required to obtain the same yield. Consequently the large scale use of endomycorrhizas has not yet been adopted in agricultural practice due to the problems of producing an inoculum which is plentiful, free of contamination, yet easy to store and easy to handle on the land.

In an attempt to resolve this problem, various studies have been carried out on the behavior in vitro of VAM fungi, associated with complete plants or roots. Although these methods are very helpful in studying the metabolism of VAM, they do appear to be uncertain as a means of producing fungus in pure culture, owing to the very slow development of the roots. Note, for example, HEPPER C. M., 1975, in *Endomycorrhizas*, Sander F. E., Mosse B. and Tinker, P. E. Eds, Acad. Press London, 67–86; MOSSE B., and HEPPER C. M., 1975, *Physiol. Pl. Pathol.*, Vol. 5, 215–225; HEPPER C. M., 1981, *New Phytol.*, Vol. 88, 641–647; MACDONALD R. M., 1981, *New Phytol.*, Vol. 89, 87–93; ST. JOHN T. V., and REID, C. P. P., 1981, *New Phytol.*, Vol. 89, 81–86.

It is known that genetic conversion of roots by insertion of a fragment of foreign DNA (known as T-DNA) from the root inducing plasmid of *Agrobacterium rhizogenes* enables aseptic cultures of roots to be formed with rapid and indefinite growth in a simple medium. Compare TEPFER D. A., 1981, *C.R. Acad. Sc. PARIS*, t. 292. Serie III, 153. *Agrobacterium rhizogenes* is the agent of a disease, i.e., hairy-root, the symptom of which is proliferation of a large number of root hairs at the point where the bacterium is inoculated.

Accordingly, it is an object of the present invention to overcome the problems of producing endomycorrhizas on a commercial scale by providing a successful method for production thereof.

It is another object of the present invention to overcome the aforenoted problems by using the new powers conferred to roots converted by the action of *Agrobacterium rhizogenes*, through inoculating cultures of such converted roots with spores of endomycorrhizas.

In particular, an object of the present invention is to provide a method of obtaining endomycorrhizas in vitro, particularly in a fermenter.

Other objects of the present invention will become readily apparent upon a review of the following description, the figures of the drawing and the claims appended hereto.

SUMMARY OF THE INVENTION

The present invention concerns a method of producing in vitro endomycorrhizian fungi with arbuscules and vesicles (VAM). The method comprises producing genetically converted dicotyledon roots by inserting genes of root inducing or tumor inducing plasmid into the genome of dicotyledon root cells, and then inoculating the converted roots with endomycorrhiza spores.

The preparation of these converted roots inoculated with endomycorrhiza spores can be more specifically divided into three steps:
- conversion of the root
- cultivation of the converted root
- mycorrhization Conversion of the root can take place as spelled out in the foregoing by transferring genes of Ri plasmid from *Agrobacterium rhizogenes* into the genome of the root cell. The culture medium for the bacterium *Agrobacterium rhizogenes* for the bacterium carrying the inducing plasmid may be of any appropriate known type, such as the medium Yeast Extract Mannitol (as in VINCENT, 1970, A Manual for Practical Study of Root Nodule Bacteria IBP Handbook No. 15), or the medium Sucrose, Nutrient Broth, Yeast Extract (as in ANAND V. H., 1977, *American Journal of Botany*, Vol. 64 (2) 153–158).

The genes of the root-inducing plasmid may be provided in several ways, either directly by the bacterium *Agrobacterium rhizogenes*, a virulent plasmid carrier, or indirectly by a bacteria to which the root-inducing plasmid has been transferred by conjugation or to which T-DNA has been transferred by conversion.

The present invention also encompasses the procedure of providing or producing roots of dicotyledons which have been genetically converted by inserting genes of the tumor inducing plasmid from *Agrobacterium tumefaciens* in the genome of said roots, and then inoculating the converted roots with endomycorrhiza spores. The genes of the tumor inducing plasmid may equally be provided in several ways, either directly by the bacterium *Agrobacterium tumefaciens*, a virulent carrier of the plasmid, or indirectly by a bacterium to which the tumor inducing plasmid has been transferred, e.g., by conjugation, or to which T-DNA has been transferred by conversion.

In the case of employing root inducing plasmid, the inducing agent, which is the plasmid, may be transferred from the *Agrobacterium rhizogenes* strain to an *Agrobacterium tumefaciens* strain. This is the case e.g., of the transconjugant C 58 Cl (pTi 8196). Compare, CHILTON M. D., *Nature*, 1982, Vol. 295, 432.

In the case of employing tumor inducing plasmid, the inducing agent, which is the plasmid, may be transferred from the virulent *Agrobacterium tumefaciens* strain to a non-virulent *Agrobacterium tumefaciens* strain, as in the case, e.g., of the transconjugant K 57, (pTi C 58). Compare, KERR A., 1977, *Nature*, Vol. 265, 560. Alternatively, transfer may be to a *Rhizobium* strain, as in the case, e.g., of the transconjugant *Rhizobium trifolii* strain, (pTi D 63). Compare, HOOYKAAS P. J. J., 1977, *J. Gen. Microbiol.* Vol. 98, 477–484. The transfer might also be to a strain of *Escherichia coli*, as in the case, e.g., of the transconjugant K 12 (pTi RP 4). Compare, HOLSTERS M., 1978, *Molec. Gen. Genet.*, Vol. 163, 335–338. Only in the last instance has the transfer of the inducing agent still not been actually checked.

The physiology of the converted roots is different from that of the non-induced ones. The changes brought about are due to insertion of a fragment of DNA from the root inducing and tumor inducing plasmid of *A. rhizogenes*, *A. tumefaciens*, or of the transconjugants used. See, CHILTON M. D., et al. 1982, *Nature*, Vol. 295, 432. The potential of the host plant is changed following the introduction of the foreign genes carried by the root inducing or tumor inducing plasmid into the genome of the root.

The converted roots may in particular be prepared by the method described by TEPFER (1981), which comprises inducing them to form from a seed or from an explant such as tubercles, stem fragments or roots. A young plantlet may also be used as described by JAYNES, see, J.M. 1981, in *Biology of Rhizobiaceae*. Eds., KENNETH L. GILLES, Acad. Press, LONDON, p. 109.

The following plants are preferred plants on which converted roots have readily been induced, i.e., the carrot, potato, soya bean, haricot bean, clover, chicory, kalanchoe ginger and bindweed, all plants belonging to the dicotyledon family.

After introducing T-DNA from the bacterium into the genome of seeds or explants, an effort is made to eliminate the inducing bacterium, which is no longer of any use. To eliminate the inducing bacterium in order to obtain aseptic cultures of converted roots, a suitable procedure is to use an antibiotic, thereby inhibiting growth of the bacterium, such as carbenicillin as described by NEISH G. A., (1975, *Mycologia*, Vol. 67), which takes account of the fact that the root system develops more rapidly than the bacterium and that the new roots develop without the bacterium. It then becomes possible to isolate the roots without the inducing agent.

The second step in the preparation of the mycorrhizated converted roots follows inoculation of seeds or explants and the appearance of roots. It comprises developing the converted roots into an aseptic culture over a simple nutritive medium without the inducing bacterium. The capacity of the converted roots to grow remains stable and permanent in the absence of the inducing bacterium.

The culture media employed for cultivation of the converted roots may be characterized as follows. There is generally an aseptic synthetic medium, either a gelose or a liquid, containing the normal macro and micro-elements, a sugar, advantageously saccharose, and one or more vitamins, preferably thiamine. The medium does not contain any phytohormone compounds. In the case of liquid media the pH is advantageously controlled. The medium may also be advantageously renewed during growth (culture).

Thus the converted roots may be put into a culture on an inorganic Monnier medium, see, *Rev. Cyt. Biol. veg.*, Vol. 39, 1976, p.1, saccharose, Morel vitamins, see GOLDMANN A., *Ann. Sc. Nat. Bot.* PARIS, Vol. 11, 1970, p. 223. The medium of MURASHIGE T. and SKOOG F., may be used, see, *Physiol. Plant.*, Vol. 15, 473–597, 1962. For some plants such as bindweed, appropriate media have been described, such as the BONNER medium modified by TORREY J. G., see *Plant physiol*, Vol. 33, 258–263, 1958.

The culture may be carried out industrially or in a manner that is completely unexpected for roots, i.e., in a fermenter. When a fermenter is used, growth takes place very rapidly, but the culture medium must be properly aerated in order to avoid anoxia of the roots. Cultivation in a fermenter is performed advantageously at ambient temperature (e.g., 20°–30° C.).

Contrary to most tests carried out on a culture of non-converted roots, the converted roots show no auxotrophia vis-a-vis phytohormonal compounds. They do form many secondary branches and have high grid potential. It is in fact necessary to use hormone compounds of the auxin type to control formation of side roots on non-converted roots.

The converted roots developed in aseptic culture thus provide a privileged symbiotic partner for the endomycorrhizian fungus, and the number of infection points on the fungus is known in particular to be increased by the appearance of any secondary roots. Compare, SMITH S. E. and WALKER N. A., 1981, *New Phytol*, Vol. 89, 225-240.

The individuals regenerated from a converted root constitute a clone of roots which have undergone a permanent, stable physiological change. The converting element, consisting of insertion of foreign genes, is replicated in the course of cellular mitosis.

Not any root clone is necessarily the host adapted to the culture process and mycorrhization, considering the T-DNA is at present thought capable of entering different parts of the genome of vegetable cells, thus giving different root clones. It is believed that no one is aware of either the entry mechanisms or the entry sites, but every clone obtained is known to be potentially more or less favorable to the formation of a culture system for converted and mycorrhized roots. Thus, the vegetable system which has the most favorable intrinsic capacity for growth must be selected.

A culture system for roots converted genetically by insertion of foreign DNA is a symbiotic partner which is far more favorable to the development of endomycorrhizas than a system of non-converted roots would be. The advantages are as follows:

1. The converted root culture system is simple and involves only the inducing effect of the bacterium *Agrobacterium rhizogenes*, or *Agrobacterium tumefaciens* or of bacteria carrying the inducing plasmid.

2. Development of converted roots is possible on a simple culture medium in an aseptic condition, and does not show any auxotrophia vis-a-vis hormone compounds.

3. There are more entry points of the VAM fungus on a converted root than on a non-converted one. The entry points on the root are known to be limited to well defined zones, and the young regions of the root towards the apex are known to be 10 times more infectible than the rest of the root. One of the characteristics of converted roots is the formation and culture of many secondary roots. The probability of new secondary entry points appearing is thus increased in the case of converted roots.

4. The high and indefinite development potential of converted roots makes it possible to obtain mass production of mycorrhized roots in culture.

5. The new potentialities of roots converted by the introduction of procaryotic genes, favorable to the infection and development of an endomycorrhizian fungus, are permanent and stable.

The third step in the process of the present invention for preparing converted roots inoculated with endomycorrhiza spores with vesicles and arbuscules comprises mycorrhizing the converted roots using endomycorrhiza spores. This step can be divided into four phases:
- isolation of the spores
- sterilization of the spores
- germination of the spores
- infection of the root Spores usable for mycorrhization are those that are easily isolated from emdomycorrhiza sporocarps taken from the roots of mycorrhizated plants. Spores that are easy to use are preferred, i.e., large-sized spores (0.1 to 1 mm., easily sterilizable). Particularly useful are the spores of *Glomus mossae*, available from Abbott Laboratories, Chemical and Agricultural Products Division, 1400 Sheridan Road North, Chicago, Ill. 60064 U.S.A., and *Gigaspora margarita*, also available from Abbott Laboratories.

The roots must be inoculated with sterile endomycorrhiza spores. To obtain sterile endomycorrhiza spores one can use any system capable of eliminating the contaminating agents and not destroying the spores. A mixture of chloramine T and streptomycin described by *MOSSE B.* may be used for this purpose. See, *Trans. Prit. Mycol. Soc.*, Vol. 42, 273-286, 1959. After being sterilized, the spores are rinsed in water and germinated.

The germination of these spores is not an easy process. However, the inhibition of germination is easily removed through the presence of microorganisms, notably mushrooms such as *Sporotrix shenkii*, or an actinomycete deposited with the C.B.S. (Centraalbureau voor Schrimmelcultures, Oosterstraat 1, P.S. Box 273, Baarn, The Netherlands) under the number 355.83.

It is practical to cultivate the inhibition-removing microorganism on an appropriate medium. It is then enclosed in an agar gel. Over this first layer of agar is poured a second layer of sterile agar. Onto this second layer are placed sterile endomycorrized spores. Germination occurs rapidly.

The inhibition-removing microorganism must not invade the upper layer of gelose and contaminate the endomycorrhiza spores. It would seem that it acts through one or more chemical substances crossing the gelose and enabling the spores to germinate.

When pregerminated spores and a root system from a culture produced, for example, in a fermenter are being used, the roots must be infected. This is done on a culture medium, e.g., gelose or liquid, containing no elements that are toxic to the infection. A long-held dogma holds that high concentrations of phosphorus inhibit the infection of the roots of whole plants. Compare, Rhodes, 1980, *Outlook Agriculture*, Vol. 10, 275-281. Contrary to this technical prejudice, however, even high concentrations of phosphorus, e.g., 170 ppm of $KH_2PO_4$, do not inhibit the process of infection of converted roots. Mineral nitrogen present in the culture media described above, however, totally inhibits the infection process.

Certain elements encourage infection of the roots. Calcium is favorable to the infection process, as are certain complexing agents. EDTA is favorable when added in low concentrations. EDTA may be replaced with other complexing agents, such as peat. The absence of root hair also encourages infection of the converted roots. The pH of the medium in which the infection takes place is advantageously between 6 and 8.

The composition of media compatible with infection may vary greatly since the initial ratios of elements such as carbon, nitrogen, calcium, and phosphorus are modified or immobilized by the growing converted root.

The converted root may also be developed toward an infection with medium placed in a compartment isolated from the nutritive medium of the root, with this infection medium consisting solely of agar and water.

In order to further illustrate the present invention and the advantages thereof, the following examples are given, it being understood that same are intended only as being illustrative and in nowise limitative.

EXAMPLE 1

(a) *Agrobacterium tumefaciens*, GRAM negative, belongs to the family of rhizobiaceae. The strain used is C 58 (strain of the PEABAGER COLLECTION, Department of Molecular Cell Biology section Microbiology. Transitorium III Padualaan 8. De Uithoi. 3584 CH Utrecht Netherlands).

(b) *Agrobacterium rhizogenes*, GRAM negative, belongs to the family of rhizobiaceae. The strain used is 8196 (strain from the NCPPB collection, National Collection of plant Pathogenic Bacteria, Plant Pathology Laboratory, Ministry of Agriculture Fisheries and Food, Eatching Green, Harpenden, Herts, ENGLAND).

The two strains were cultivated in liquid medium YEM.

Root induction. Potato or carrot tubercles were sterilized by immersion in a mercuric chloride (0.1%) or a sodium hypochlorite (1.05%) solution for 5 mins., then rinsed with sterile water 10 times. Discs 10 mm in diameter and 4 mm high were cut out under sterile conditions with a punch and placed on a gelose medium (Agar DIFCO 1%).

The discs were inoculated with 0.1 ml of bacteria culture (at $10^\circ$/ml). About two weeks after inoculation, roots appeared on most of the explants inoculated with strain 8196, and on some explants inoculated with strain C 58. Segments of roots were separated from the potato or carrot disc, rinsed by steeping several times in sterile water and placed on the MONNIER-MOREL medium, which had carbenicillin incorporated in it (600 mg/l). The roots which continued to develop on the medium formed a large number of absorbent fur-like pieces, giving the appearance of white, downy felting at the roots. The roots were again rinsed with sterile water and transferred to the nutrient medium without the antibiotic.

As soon as the roots were developed on the gelose or liquid medium, the cultures were subcultured at intervals of approximately two weeks.

Composition of culture medium. The medium was made up of the inorganic MONNIER medium, a MOREL vitamin solution and saccharose (3%); the pH was adjusted to 6.0.

| INORGANIC MONNIER MEDIUM | | | | |
|---|---|---|---|---|
| Macro-elements | | | Micro-elements | |
| Salts | mg/l | mM/l | Salts | mg/l |
| $NH_4NO_3$ | 1650 | 20.8 | $H_3BO_3$ | 8.2 |
| $KNO_3$ | 1900 | 18.8 | $MnSO_4, 4H_2O$ | 22.3 |
| $CaCl_2, 2H_2O$ | 440 | 3.0 | $ZnSO_4, 4H_2O$ | 8.6 |
| $MgSO_4, 7H_2O$ | 370 | 1.5 | KI | 0.83 |
| $KH_2PO_4$ | 170 | 1.2 | $NaMoO_4, 2H_2O$ | 0.25 |
| $Na_2EDTA$ | 37.3 | 0.1 | $CuSO_4, 5H_2O$ | 0.025 |
| $FeSO_4, 7H_2O$ | 27.8 | 0.1 | $CuCl_2, H_2O$ | 0.025 | mM = millimole

MOREL vitamins. Calcum pantothenate: 1 mg/l; inositol: 100 mg/l; biotin: 0.01 mg/l; nicotinic acid: 1 mg/l; pyridoxin: 1 mg/l and thiamine: 1 mg/l.

The BONNER medium modified by TORREY was used for the culture of converted bindweed roots.

in mg/l: $Ca(NO_3)_2$ $4H_2O$ 242; $MgSO_4$ $7H_2O$ 42; $KNO_3$ 85; KCl 61; $KH_2PO_4$ 20; $FeCl_3$ 1.5; Thiamine HCl 0.1; nicotinic acid 0.5; $ZnSO_4$ 1.5; $MnSO_4$ 4.5; $Na_2MoO_4 2H_2O$ 0.25; $H_3BO_3$ 1.5; $CuSO_4$ 0.004; and, saccharose 40,000. The pH was 5.0.

The media used for cultures of converted roots of potato, carrot, or bindweed did not permit infection of endomycorrhiza.

EXAMPLE 2

Culture in fermenter:

Culture of the converted roots in a liquid medium was effected in a 2 and 30 liter autoclavable Biolafitte fermenter of the cell culture type, as follows:

medium: MONNIER-MOREL medium adjusted to pH 5.8, filling: 750 ml for the 2 liter fermenter and 20 for the 30, fermentation unit sterilized in autoclave for 30 minutes at 115° C.; pH after sterilization was 5.3, after being cooled, the medium was seeded with a preculture in a Petri dish of converted convolvulus (bindweed) roots. The medium was agitated with a turbine of the cell culture type, turning at 50 rpm and aerated with an air flow of 80 l/h at a pressure of $0.1 \cdot 10^5$ Pa; the fermentation temperature was set to 25° C.

It was possible to proceed in a similar way without the turbine, aeration being carried out simply by bubbling through the air. In both cases, the volume of the fermenter was colonized by the converted roots in two to three weeks.

The culture media was seeded with converted roots which were kept in a Petri dish for several months at 4° C.

Production expressed in term of dry matter was 13.4 g/l in 17 days.

EXAMPLE 3

Obtaining sterile spores of *Glomus mosseae*:

The endogonacea used was a *Glomus Mosseae* strain from the laboratory of B. MOSSE (Rothmansted) (Department of soil microbiology—Rothmansted experimental station. HARPENDEN HERTFONDSHIRE—ENGLAND AL5 2JC). Glomus strains are available from Abbott Laboratories Chemical and Agricultural Products Division, 1400 Sheridan Road N. Chicaco, Ill. 60064 U.S.A.

To obtain a high number of sporocarps, the composition of the culture substratum for the host plant was as follows: vermiculite, perlite, and a low-phosphorus soil of Fontainebleau in proportions of 5:5:1. The pH of the mixture was 6.5. After two vegetation periods (6 months), the number of sporocarps was approximately 10,000 per liter of substratum.

Isolation of the spores:

Onions which were mycorrhized with *Glomus mosseae* and well developed were unpotted. Under a binocular magnifying glass, sporocarps measuring 0.1 to 1 mm in diameter were picked out directly with a pipette and placed in a Petri dish on moist filter paper. The spores formed inside the sporocarps were then extracted with a needle. Each sporocarp provided 1 to about 100 spores. The spores were kept at 4° C.

Spore sterilization:

The sterilizing mixture used was made up of streptomycin, dichloramine T (2%) and a few drops of Tween 80. The procedure for sterilizing the spores included two stages.

In the first stage, a wire mesh filter ($\emptyset < 50$ μm) was placed in a millipore column, and 500 ml of the sterilizing mixture was passed over the spores.

In the second stage, the wire resin filter was replaced by a MILLIPORE paper reference AW 03 04 700) in the Millipore column mounted over a flask under vacuum.

500 ml of sterilizing mixture was passed over the spores, suspended in the top of the column, and the liquid level was kept at approximately 2 cm above the Millipore paper, with constant agitation. After this treatment the spores were rinsed six times with sterile water. At the last rinse the Millipore paper was dried by pumping for longer; the spores were removed under sterile conditions and transferred to the rich nutrient medium as a check on sterility.

Germination of the spores:

The germination-inducing microorganism (actinomycete deposited at C.B.S. under no. 355.83) was cultivated in a liquid medium and shaken. It contained the following elements: glucose 10 g/l, yeast extract 2 g/l, and water to make one liter.

Pellets of this microorganism were obtained. They were washed and enclosed in Agar Difco gelose at 0.5%. Over this gelose was poured a second layer of agar and onto this layer was placed the sterile Endomycorrhiza spores. In 10 to 15 days, approximately 100% germination was obtained (FIG. 1).

Figure 1:
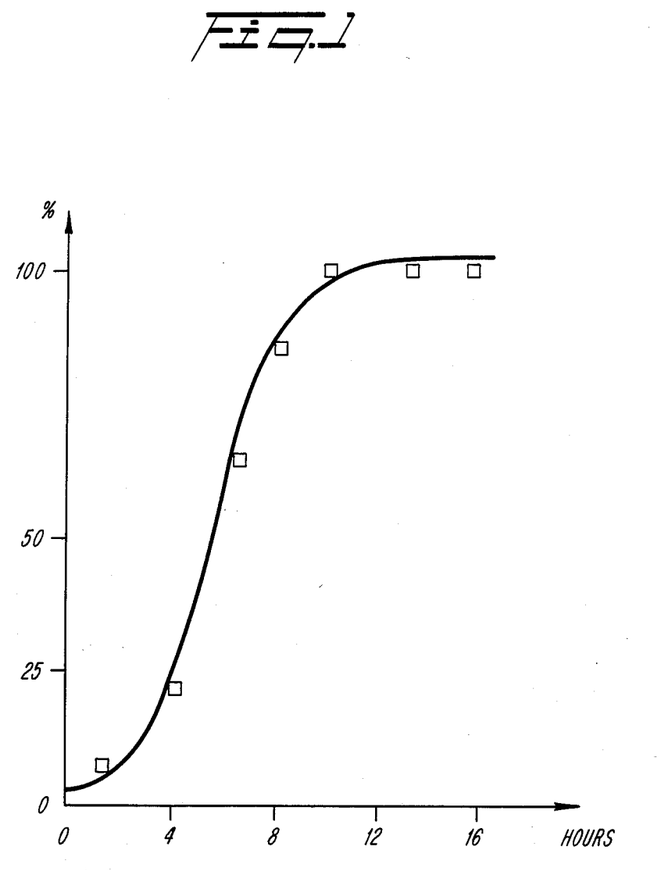

FIG. 1 represents the percentage of germination of spores placed on the 0.7% Agar Difco gelose medium in the presence of actinomycete number 355.83, as a function of time expressed in days. (The control batch placed on the same gelose medium but without bacteria did not yield any germinated spores.) Only the spores or very distinct lipid globules germinated.

Figure 2:
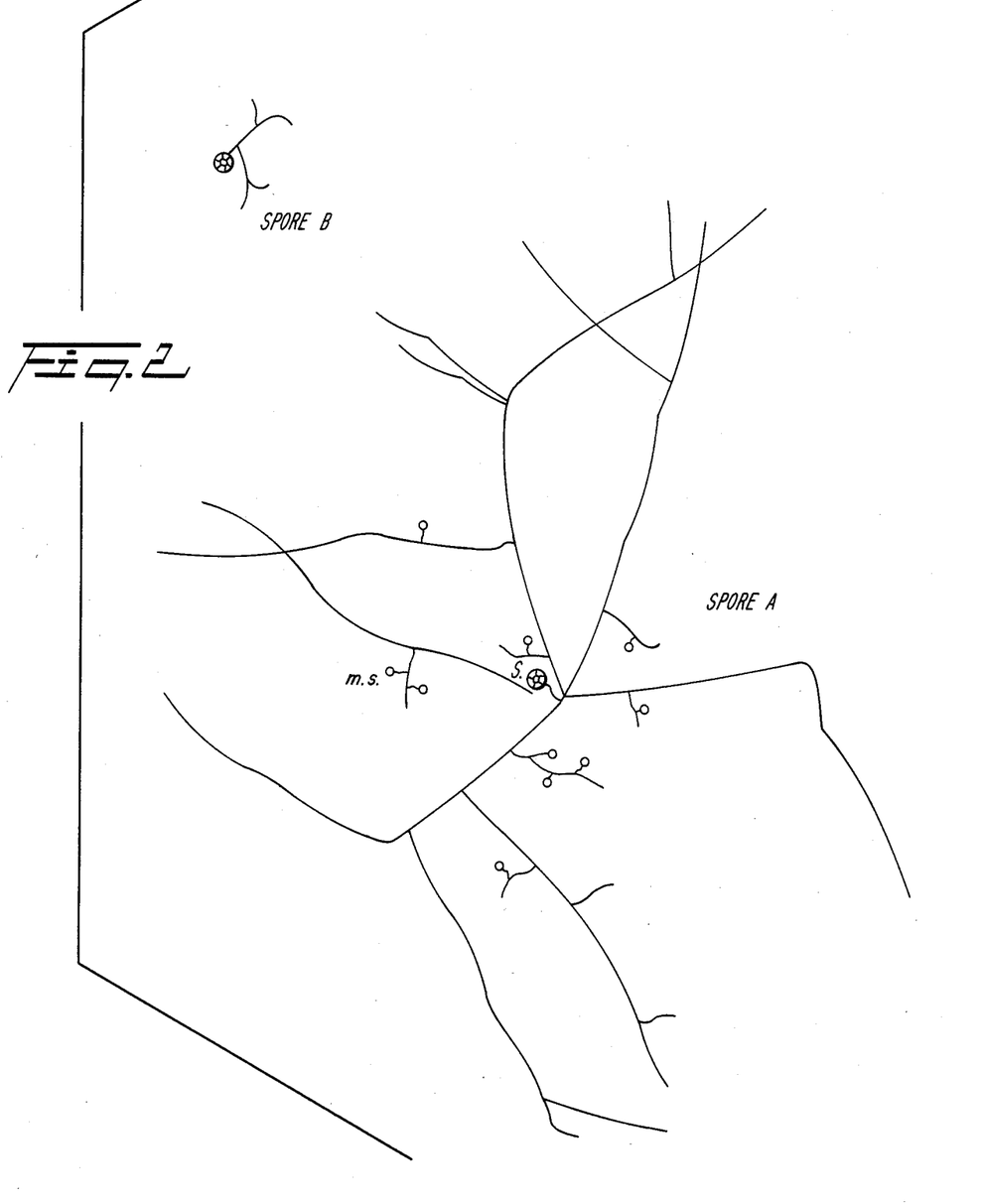

The spore was considered to have really germinated when the germination process was as follows:

A mycelial filament emerged from what remained of the old attachment hypha. It then spread and vegetative microspores appeared on the hyphas. FIG. 2 illustrates this process schematically.

FIG. 2 shows:
- a spore A that has germinated in the presence of an actinomycete (m.s. means vegative microspore; h=hypha; s=spore).
- a spore B placed on a gelose medium without actinomycete.

The germination-inducing microorganism does not develop in the system described and thus does not invade the gelose layer over which the spores are placed. However, it remains capable of producing one or more unknown substances that remove the inhibition to germinate.

Infection of the root:

The pregerminated spores were placed in proximity to a *Convolvulus sepium* root with very little root hair, placed on a nitrogen-poor medium low in elements toxic for the growth of mycelium such as zinc, manganese, or mineral nitrogen in large quantities. The medium contained stimulants such as calcium and EDTA. Infection of the bindweed root was very rapid, with the first infectious structures observable three days after the spore was deposited.

The first mycelial structures characteristic of a mycorrhiza VA infection following deposit of the spore consisted of fan-like structures that developed, after about 10 days, toward the formation of arbuscules in the cells of the converted root.

Method for coloration of fan-like and arbuscular structures:

Fragments of converted roots 2 cm long were taken and lightened by a 20% KOH solution for one hour in an oven at 90° C. Complete bleaching of the samples was obtained in a 5% aqueous solution of $H_2O_2$ with 30 volumes. The samples were colored either by a 0.05% solution of trypan blue in Amann lactophenol for 5 minutes hot, or in a 0.1% solution of fuschic acid in a mixture of water and acetic acid (1 v/10 v) for 2 minutes. The second method tended to cause substantial deterioration in fungal structures, but on the other hand allowed for better differentiation between fungus and root cells. After being colored, the samples are washed and mounted with lactophenol.

Figure 3:
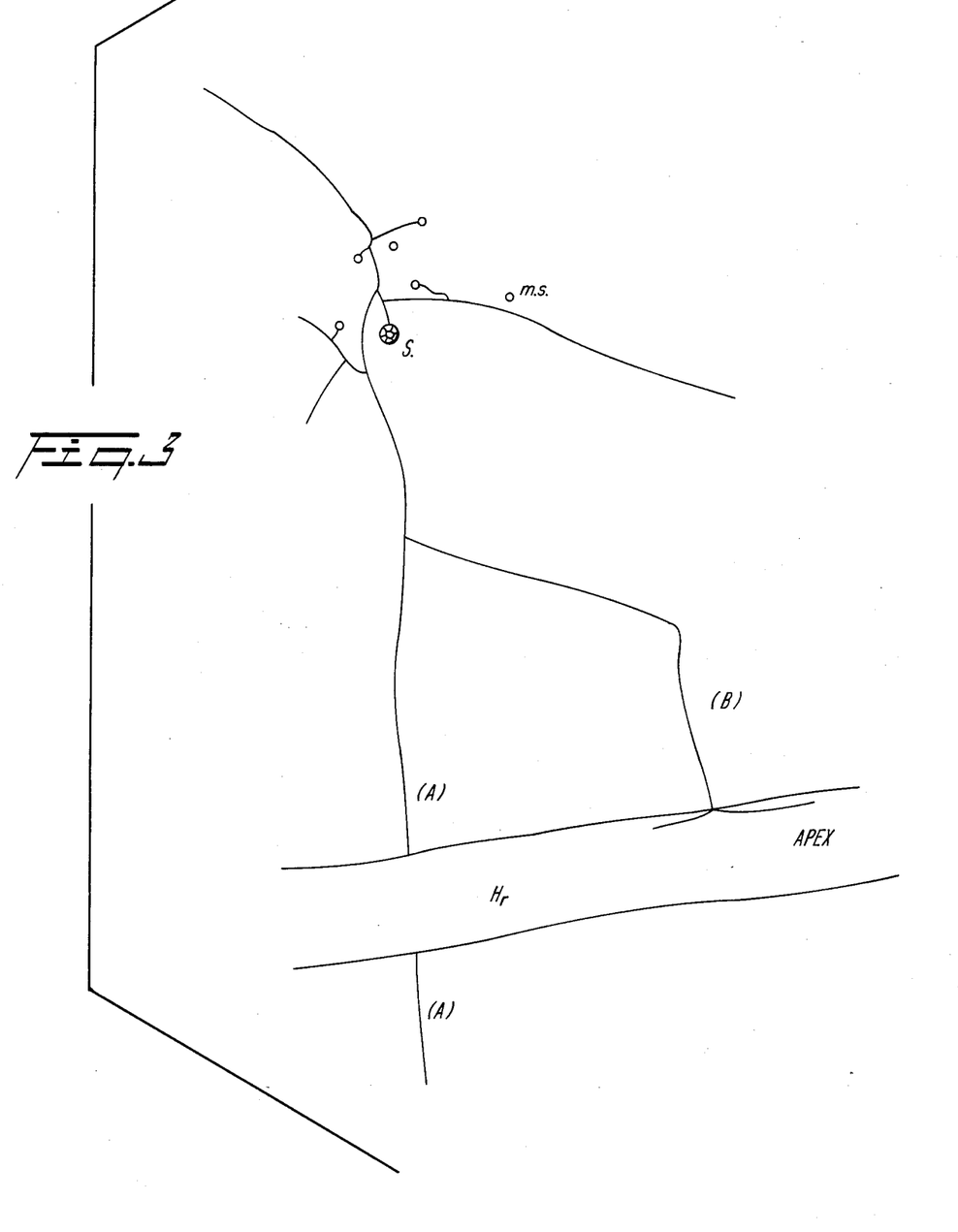

FIG. 3 shows a mycelial filament spread into two branches, one of which (a) passes under the converted root while the other (b) infects it.

Figure 4:
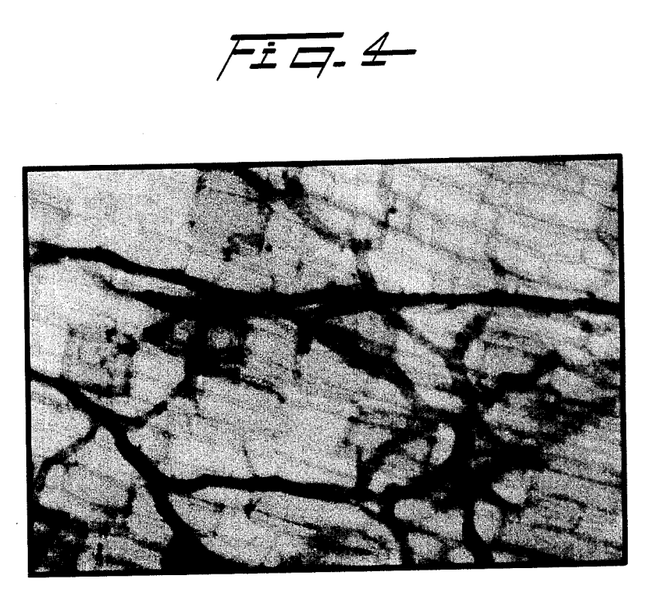

FIG. 4 is a photograph taken with a photon microscope. It shows the first phase of infection of a converted root of *Convolvulus sepium* after three days, with the characteristic fan-like, compartmentalized structures of the mycelium.

Figure 5:
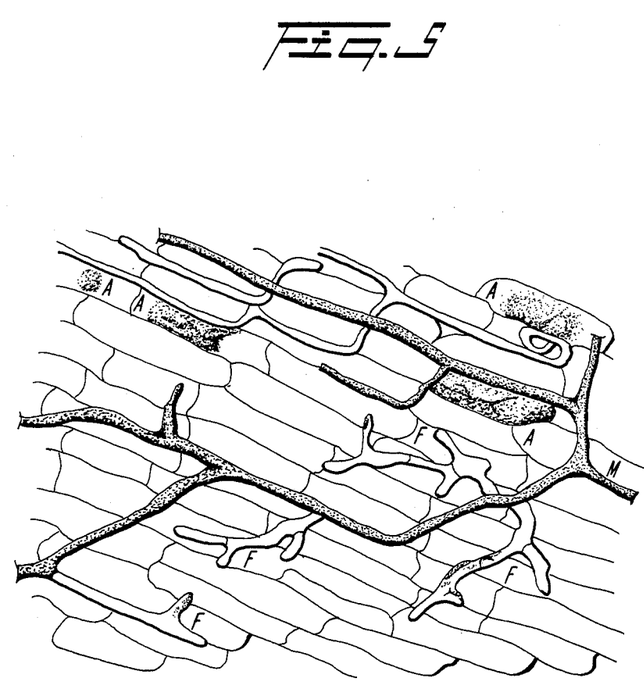

FIG. 5 is a drawing representing the second phase of infection, after 10 days, with formation of arbuscules. In the figure:
M represents the mycelium
F represents the fan-like structures
A represents the arbuscles.

While the invention has now been described in terms of various preferred embodiments and illustrated with respect to certain examples, it will be apparent to the skilled artisan that various omissions, substitutions, modifications and the like may be made without departing from the spirit of the invention. Accordingly, it is intended that the scope of the present invention be limited only by the following claims.

What is claimed is:

1. A method of producing endomycorrhiza fungi with arbuscules and vesicles in vitro comprising:
   (a) transforming dicotyledon roots with a bacterium containing a root-inducing plasmid, wherein T-DNA of said plasmid becomes integrated into the root cell chromosome;
   (b) cultivating the transformed root cells aseptically;
   (c) inoculating said transformed root cells with endomycorrhiza spores.

2. The method of claim 1 wherein said bacterium is *Agrobacterium rhizogenes*.

3. The method of claim 1 wherein said root-inducing plasmid has been transferred from *A. rhizogenes* to a second bacterium prior to transforming the roots.

4. The method of claim 1 wherein said root cells are induced to form from a dicotyledon seed or explant and said cultivation step occurs on a minimal medium.

5. The method of claim 1 wherein the endomycorrhiza belongs to the Endogonaceous family.

6. The method of claim 1 wherein the endomycorrhiza is a *Glomus mosseae*.

7. The method of claim 1 wherein the transformed root cells are cultivated aseptically on a minimal medium without any hormone compounds and which medium comprises a sugar and at least one vitamin.

8. The method of claim 7 wherein the sugar comprises saccharose.

9. The method of claim 7 wherein the vitamin comprises thiamine.

10. The method of claim 9 wherein the sugar comprises saccharose.

11. The method of claim 7 wherein the transformed root cells are cultivated on a gelose medium.

12. The method of claim 7 wherein the transformed root cells are cultivated in a liquid medium.

13. The method of claim 12 wherein the transformed root cells are cultivated in a fermenter having an aerated medium.

14. The method of claim 1 wherein germination of the spores is enhanced by a microorganism.

15. The method of claim 14 wherein said microorganism is *Sporotrix shenkii* or an actinomycete.

16. The method of claim 1 wherein inoculation of said transformed root cells with said endomycorrhiza spores is carried out in the presence of calcium and a complexing agent and on a medium having a pH of between 6 and 8 which is free of toxic compounds and low in mineral nitrogen.

17. The method of claim 16 wherein there is an absence of root hair on the root.

18. The method of claim 16 wherein the medium is free of manganese and zinc.

19. The method of claim 16 wherein the complexing agent is EDTA.

20. A method of producing endomycorrhiza fungi with arbuscules and vesicles in vitro comprising:
    (a) transforming dicotyledon roots with a bacterium containing a tumor-inducing plasmid, wherein T-DNA of said plasmid becomes integrated into the root cell chromosome;
    (b) cultivating the transformed root cells aseptically;
    (c) inoculating said transformed root cells with endomycorrhiza spores.

21. The method of claim 20 wherein said bacterium is *Agrobacterium tumefaciens*.

22. The method of claim 20 wherein said tumor-inducing plasmid has been transferred from *A. tumefaciens* to a second bacterium prior to transforming the roots.

23. The method of claim 20 wherein said root cells are induced to form from a dicotyledon seed or explant and said cultivation step occurs on a minimal medium.

24. The method of claim 20 wherein the endomycorrhiza belongs to the Endogonaceous family.

25. The method of claim 20 wherein the endomycorrhiza is a *Glomus mosseae*.

26. The method of claim 20 wherein the transformed root cells are cultivated aseptically on a minimal medium without any hormone compounds and which medium comprises a sugar and at least one vitamin.

27. The method of claim 26 wherein the sugar comprises saccharose.

28. The method of claim 26 wherein the vitamin comprises thiamine.

29. The method of claim 28 wherein the sugar comprises saccharose.

30. The method of claim 26 wherein the transformed root cells are cultivated on a gelose medium.

31. The method of claim 26 wherein the root cells are cultivated in a liquid medium.

32. The method of claim 31 wherein the transformed roots cells are cultivated in a fermenter having an aerated medium.

33. The method of claim 20 wherein germination of the spores is enhanced by a microorganism.

34. The method of claim 33 wherein said microorganism is *Sporotrix shenkii* or an actinomycete.

35. The method of claim 20 wherein said inoculation of said transformed root cells with said endomycorrhiza spores is carried out in the presence of calcium and a complexing agent and on a medium having a pH of between 6 and 8 which is free of toxic compounds and low in mineral nitrogen.

36. The method of claim 35 wherein there is an absence of root hair on the root.

37. The method of claim 35 wherein the medium is free of manganese and zinc.

38. The method of claim 35 wherein the complexing agent is EDTA.

39. A method of producing endomycorrhiza fungi with arbuscles and vesicles in vitro comprising inoculating dicotyledon roots transformed with T-DNA with endomycorrhiza spores.

* * * * *